United States Patent
Elgas et al.

(10) Patent No.: US 6,613,279 B1
(45) Date of Patent: Sep. 2, 2003

(54) METHOD AND APPARATUS FOR IMPROVING BLOOD MIXING IN OXYGENATORS

(75) Inventors: Roger J. Elgas, Anaheim Hills, CA (US); Robert F. Gremel, Huntington Beach, CA (US)

(73) Assignee: Medtronic, Inc., Brooklyn Park, MN (US)

( * ) Notice: Subject to any disclaimer, the term of this patent is extended or adjusted under 35 U.S.C. 154(b) by 0 days.

(21) Appl. No.: 09/386,245

(22) Filed: Aug. 31, 1999

(51) Int. Cl.[7] ................ A61M 1/14; A61M 37/00
(52) U.S. Cl. ..................... 422/45; 604/6.14
(58) Field of Search ............... 422/44–48; 210/321.8; 604/6.14

(56) References Cited

U.S. PATENT DOCUMENTS

| | | | |
|---|---|---|---|
| 3,228,877 A | 1/1966 | Mahon | 210/22 |
| 3,422,008 A | 1/1969 | McLain | 210/22 |
| 3,690,465 A | 9/1972 | McGinnis et al. | 210/321 |
| 3,794,468 A | 2/1974 | Leonard | 23/258.5 |
| 3,801,401 A | 4/1974 | Cope et al. | 156/172 |
| 3,927,980 A | 12/1975 | Leonard | 23/258.5 |
| 3,998,593 A | 12/1976 | Yoshida et al. | 23/258.5 |
| 4,080,296 A | 3/1978 | Clark | 210/323 R |
| 4,311,589 A | 1/1982 | Brumfield | 210/177 |
| 4,451,562 A | 5/1984 | Elgas et al. | 435/2 |
| 4,455,230 A | 6/1984 | Elgas et al. | 210/232 |
| 4,572,446 A | 2/1986 | Leonard et al. | 242/7.02 |
| 4,666,469 A | 5/1987 | Krueger et al. | 55/16 |
| 4,689,255 A | 8/1987 | Smoot et al. | 428/77 |
| 4,690,758 A | 9/1987 | Leonard et al. | 210/247 |
| 4,707,268 A | 11/1987 | Shah et al. | 210/650 |
| 4,735,775 A | 4/1988 | Leonard et al. | 422/46 |
| 4,770,778 A | 9/1988 | Yokoyama et al. | 210/321.79 |
| 4,781,834 A | 11/1988 | Sekino et al. | 210/321.88 |
| 4,818,490 A | 4/1989 | Carson et al. | 422/46 |
| 4,863,600 A | 9/1989 | Leonard et al. | 210/321.74 |
| 4,876,066 A | 10/1989 | Bringham et al. | 422/46 |
| 4,940,617 A * | 7/1990 | Baurmeister | 428/113 |
| 5,143,312 A | 9/1992 | Baurmeister | 242/7.02 |
| 5,152,964 A | 10/1992 | Leonard | 422/48 |
| 5,186,832 A * | 2/1993 | Mancusi et al. | 210/321.8 |
| 5,236,665 A | 8/1993 | Mathewson et al. | 422/46 |
| 5,240,677 A | 8/1993 | Jones et al. | 422/46 |
| 5,297,591 A | 3/1994 | Baurmeister | 139/383 R |
| 5,312,589 A | 5/1994 | Reeder et al. | 422/45 |
| 5,346,621 A | 9/1994 | Haworth et al. | 210/645 |
| 5,376,334 A | 12/1994 | Haworth et al. | 422/46 |
| 5,421,405 A | 6/1995 | Goodin et al. | 165/154 |
| 5,462,619 A | 10/1995 | Haworth et al. | 156/172 |
| 5,489,413 A | 2/1996 | Carson et al. | 422/46 |
| 5,514,335 A | 5/1996 | Leonard et al. | 422/46 |
| 5,609,632 A | 3/1997 | Elgas | 623/12 |
| 5,626,759 A | 5/1997 | Krantz et al. | 210/645 |
| 5,702,601 A | 12/1997 | Bikson | 210/321.79 |

(List continued on next page.)

FOREIGN PATENT DOCUMENTS

| | | | |
|---|---|---|---|
| DE | 654158 | 12/1937 | |
| EP | 0 299 381 | 7/1988 | |
| EP | 0 408 000 | 7/1990 | |
| EP | 0 553 488 A1 | 8/1993 | B01D/63/02 |
| EP | 0 798 035 A2 | 10/1997 | B01D/63/02 |
| FR | 2 555 724 | 11/1983 | |
| JP | 56025696 | 12/1981 | |
| WO | 83/00098 | 1/1983 | |
| WO | WO 83/00098 | 1/1983 | |
| WO | WO 97/26032 | 7/1997 | |

*Primary Examiner*—Angela D. Sykes
*Assistant Examiner*—Leslie R. Deak
(74) *Attorney, Agent, or Firm*—Stout, Uxa, Buyan & Mullins, LLP; Donald E. Stout

(57) ABSTRACT

Blood mixing in fiber-wound oxygenators is improved by inserting at least one layer of a planar apertured mat between selected layers of wound gas-exchange fibers.

3 Claims, 3 Drawing Sheets

U.S. PATENT DOCUMENTS

| | | | |
|---|---|---|---|
| 5,718,871 A | 2/1998 | Elgas | 422/46 |
| 5,747,138 A | 5/1998 | Leonard | 428/113 |
| 5,762,868 A | 6/1998 | Leonard | 422/46 |
| 5,762,875 A | 6/1998 | Gremel et al. | 422/45 |
| 5,876,667 A | 3/1999 | Gremel et al. | 422/44 |
| 5,888,611 A | 3/1999 | Leonard | 428/113 |
| 5,897,729 A | 4/1999 | Bikson | 156/172 |
| 5,906,741 A | 5/1999 | Elgas et al. | 210/455 |
| 5,922,202 A | 7/1999 | Elgas et al. | 210/456 |
| 5,922,281 A | 7/1999 | Elgas et al. | 422/45 |
| 6,045,752 A | 4/2000 | Elgas | 422/46 |
| 6,214,232 B1 * | 4/2001 | Baurmeister et al. | 210/321.75 |

* cited by examiner

METHOD AND APPARATUS FOR IMPROVING BLOOD MIXING IN OXYGENATORS

FIELD OF THE INVENTION

This invention relates to wound fiber oxygenators, and more specifically to a method and apparatus for improving the blood-fiber contact by disrupting the laminar flow of the blood across the fibers.

BACKGROUND OF THE INVENTION

A common form of blood oxygenator used in heart-lung machines consists of many layers of microporous hollow gas-exchange fibers wound at an angle around a generally cylindrical core. Oxygen is made to flow longitudinally through the hollow fibers, and blood is caused to flow across the fibers. The material of the fibers is such that whenever a blood cell contacts a fiber, an oxygen-carbon dioxide exchange takes place between the cell and the inside of the fiber.

Because the efficiency of the oxygenator depends on the number of blood cells that contact the fibers, it is desirable to thoroughly mix the blood as it flows across the fibers. This assures that the maximum number of blood cells will have a chance to get close enough to a fiber for a successful gas exchange at some point during their transit through the oxygenator.

In conventional fiber-wound oxygenators, such thorough mixing is, however, difficult to achieve. Although the fibers are wound in opposite directions in successive layers so that they cross each other, the geometry of such windings is such that channels exist in which blood can flow laminarly all the way through the fiber bundle. Even where the blood flow encounters a fiber, the flow typically divides to flow across opposite sides of the fiber, and then recombines back into a generally laminar flow.

SUMMARY OF THE INVENTION

The present invention increases mixing of the blood in a wound fiber oxygenator by disrupting laminar blood flow through the channels formed by the winding pattern of the fibers. This is accomplished in the invention by periodically inserting, between two successive layers of fibers, a generally flat, ribbed apertured sheet of plastic. Such a sheet is preferably composed of a gridwork of solid ribs running at right angles to each other in a common plane.

BRIEF DESCRIPTION OF THE DRAWINGS

FIG. 3b is a section along line 3b–3b of FIG. 3a;

DESCRIPTION OF THE PREFERRED EMBODIMENT

Figure 1:
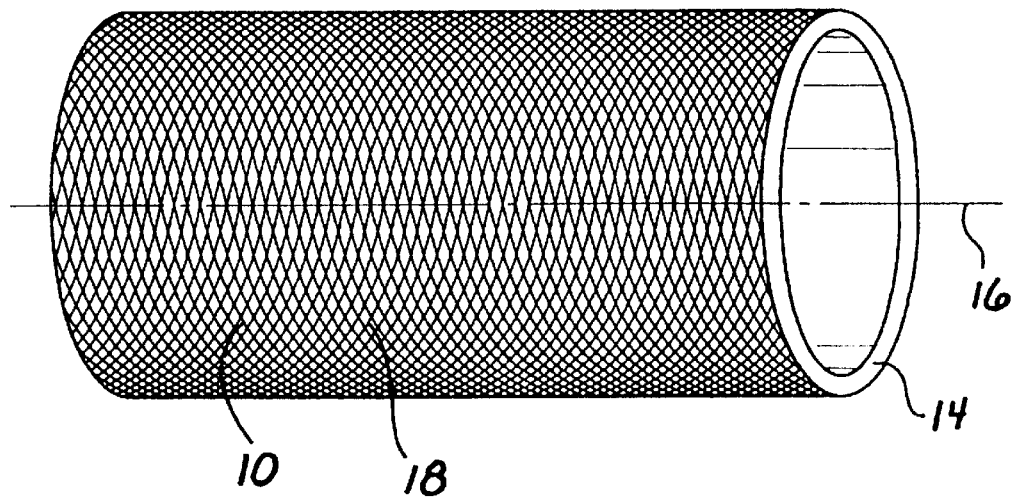
FIG. 1 is a plan view of a portion of a typical oxygenator fiber winding.

FIG. 1 illustrates a typical winding pattern for creating a fiber bundle in wound fiber oxygenators. A first layer 10 of hollow gas-exchange fibers 12 is wound on the core 14 at an acute angle to the axis 16 of the core 14. The next layer 18 of fibers 12 is wound at an obtuse angle to the axis 16, and further layers are alternated in the same manner between acute and obtuse angles. The fiber bundle thus formed is then conventionally potted and cut at each end (not shown) to form a multiplicity of individual fibers through which oxygen can be conveyed.

Figure 2:
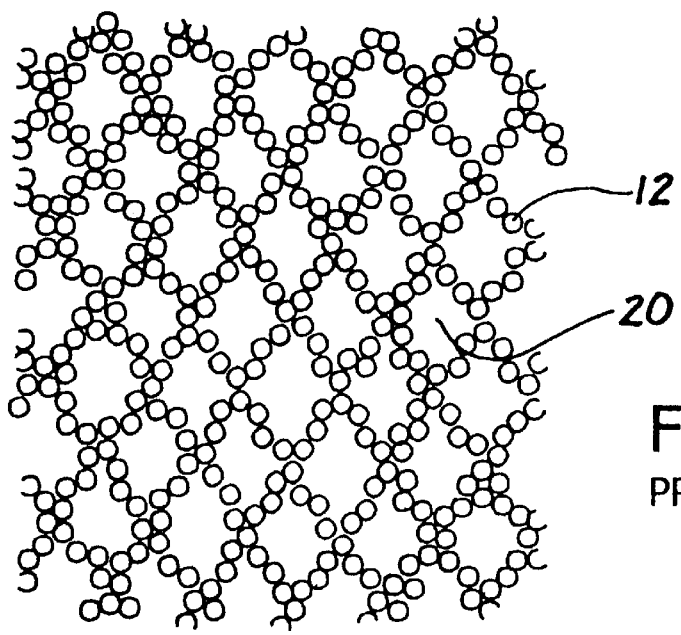
FIG. 2 is an enlarged sectional view of the winding of FIG. 1 transverse of the unobstructed flow channels therethrough.

Theoretically, blood flowing across the bundle of fibers 12 so wound will encounter sufficient direction changes while flowing around the crossed fibers 12 to mix the blood stream and expose all of its parts to oxygenation at fiber walls. In practice, however, the mixing is not as thorough as it could be. As seen in FIG. 2, the conventional winding pattern creates small channels 20 in which blood can flow laminarly. In such a laminar flow, blood cells traveling in the center of the channels 20 are less likely to encounter a gas-exchanging fiber surface than those traveling near the edges of the channels 20.

Figure 3A:
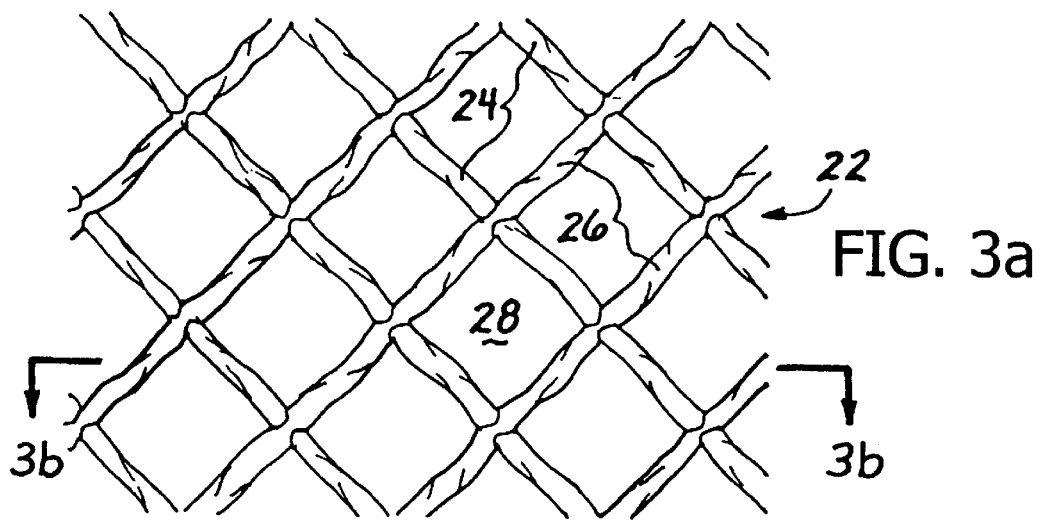
FIG. 3a is a plan view of a mat material preferred in the invention.
Figure 3B:
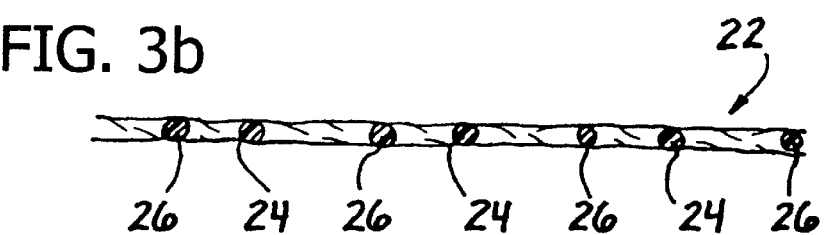

In order to break up the laminar flow of blood in the channels 20, the invention proposes placing an apertured, planar plastic mat 22 (FIGS. 3a and 3b) around the core 14 at least once during the winding of the fibers 12. Because of the planar nature of the mat 22, the mat 22 intersects the channels 20 and breaks up the laminar flow pattern through the channels 20.

The mat 22 is preferably formed of a planar, integral gridwork of plastic ribs 24, 26 intersecting each other at an angle which may be about 90° or less, which define generally, diamond-shaped apertures 28 between them. Such a material is commercially available from various manufacturers.

Figure 4:
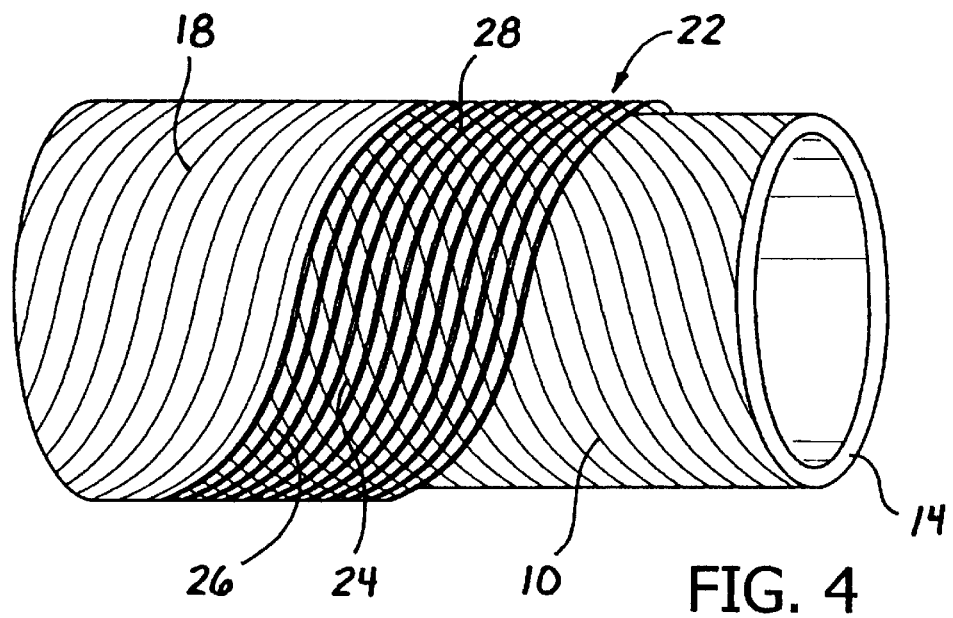
FIG. 4 is a schematic view showing the material of FIG. 3 inserted into an oxygenator fiber winding.
Figure 5A:
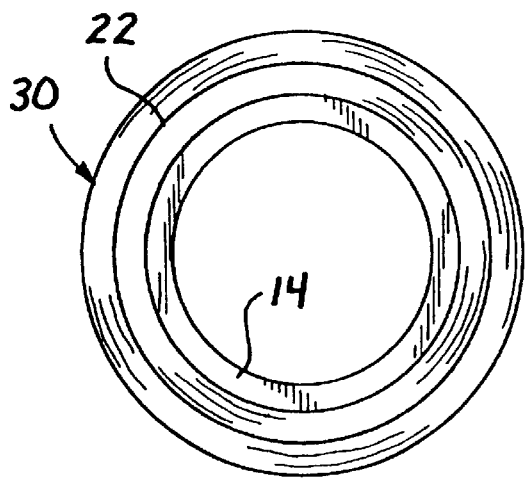
FIGS. 5a through 5c are end views illustrating preferred placements of the mat in the fiber winding.
Figure 5B:
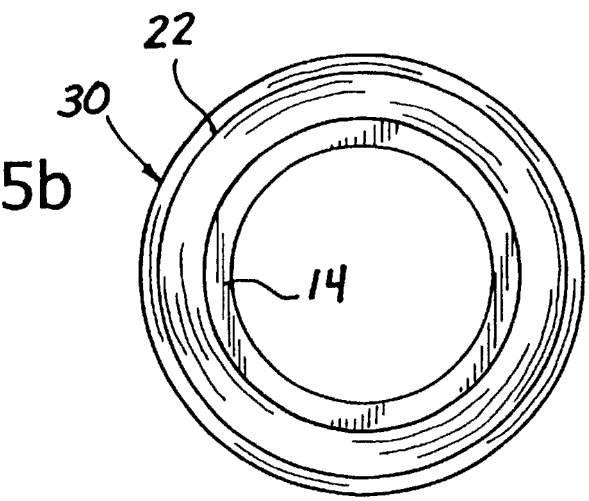
Figure 5C:
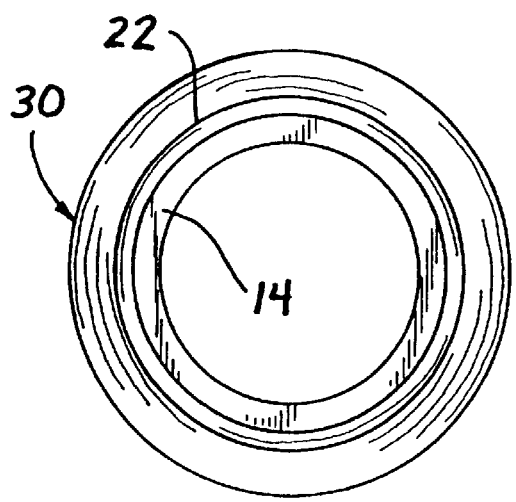

As shown in FIG. 4 (in which the spacing between the fibers 12 in the layers 10 and 18 is exaggerated for clarity), a preferred way of carrying out the invention involves winding a plurality of layers of fibers 12 onto the core 14, placing a mat 22 around the core 14, and continuing to wind more layers of fibers 12 onto the core 14. Preferably, the advantages of the invention can be obtained by a single mat 22 placed about half way (FIG. 5a), two-thirds of the way (FIG. 5b) or one-third of the way (FIG. 5c) through the winding 30. It would also be possible to place a plurality of mats 22 onto the core 14 at intervals during the process of winding the fibers 12.

Following the winding of the fibers 12, with the mats 22 inserted between fiber layers, the ends of the winding 30 can be potted, cut and processed in the conventional manner (not shown).

It is understood that the exemplary method and apparatus for improving blood mixing in oxygenators described herein and shown in the drawings represents only a presently preferred embodiment of the invention. Indeed, various modifications and additions may be made to such embodiment without departing from the spirit and scope of the invention. Thus, other modifications and additions may be obvious to those skilled in the art and may be implemented to adapt the present invention for use in a variety of different applications.

We claim:

1. A multi-layer wound-fiber blood oxygenator, comprising:
   a) a core having an axis;
   b) a first group of wound-fiber layers, including
      i) at least one layer of hollow gas-exchange fibers wound around said core at an acute angle relative said axis, and ii) at least one layer of hollow gas-exchange fibers wound around said core at an angle of at least 90° relative said axis;

c) a second group of wound-fiber layers, including
   i) at least one layer of hollow gas-exchange fibers wound around said core at an acute angle relative said axis, and
   ii) at least one layer of hollow gas-exchange fibers wound around said core at an angle of at least 90° relative said axis; and d) a planar, apertured mat positioned around said core between said first and second groups of layers, the mat consisting essentially of spaced coplanar plastic ribs intersecting each other to define apertures therebetween.

2. The oxygenator of claim 1, wherein said ribs so intersect each other as to form substantially diamond-shaped apertures between them.

3. A method of improving mixing of a blood stream while traveling through a gas-exchange fiber bundle in a wound-fiber oxygenator, comprising the steps of:

a) forming an inner portion of a fiber bundle by winding a first group of layers of hollow gas-exchange fibers around a core having an axis, the first group including
   i) at least one layer of hollow gas-exchange fibers wound around said core at an acute angle relative said axis, and
   ii) at least one layer of hollow gas-exchange fibers wound around said core at an angle of at least 90° relative said axis;

b) placing a planar, apertured mat around the inner portion of said bundle; and c) forming an outer portion of said bundle by winding a second group of layers of hollow gas-exchange fibers around the core, the second group including
   i) at least one layer of hollow gas-exchange fibers wound around said core at an acute angle relative said axis, and
   ii) at least one layer of hollow gas-exchange fibers wound around said core at an angle of at least 90° relative said axis.

* * * * *